United States Patent [19]
Baldwin

[11] Patent Number: 5,280,170
[45] Date of Patent: Jan. 18, 1994

[54] MACHINE FOR INSPECTING THE SHAPE OF A CONTAINER HAVING A TWO DIMENSIONAL CAMERA FOR VIEWING THE SHADOW OF THE PROJECTION OF THE CONTAINER

[75] Inventor: Leo B. Baldwin, Horseheads, N.Y.

[73] Assignee: Emhart Glass Machinery Investments Inc., Wilmington, Del.

[21] Appl. No.: 994,777

[22] Filed: Dec. 22, 1992

[51] Int. Cl.⁵ .............................................. G01N 9/04
[52] U.S. Cl. .................................. 250/223 B; 356/240
[58] Field of Search ... 250/223B, 223R; 356/240, 428, 356/372, 237; 209/524, 526, 538

[56] References Cited
U.S. PATENT DOCUMENTS 4,786,801  11/1988  Shay .............................. 250/223 B
4,959,537   9/1990  Kimoto et al. ...................... 356/240
5,114,230   5/1992  Pryor ................................ 356/372

Primary Examiner—David C. Nelms
Assistant Examiner—Le: Que T.
Attorney, Agent, or Firm—Spencer T. Smith

[57] ABSTRACT

An inspection machine for inspecting the outer surface of a vertically standing container comprising a transparent convey for conveying a vertically standing container through an inspection location. The support conveyor includes a diffuser plate located to be beneath a conveyed container at the inspection location. A beam of collimated light is directed vertically downwardly towards the diffuser plate, and a two-dimensional camera axially views the bottom of the container above the diffuser plate, and the image is processed to evaluate the circumference of the container.

4 Claims, 1 Drawing Sheet

MACHINE FOR INSPECTING THE SHAPE OF A CONTAINER HAVING A TWO DIMENSIONAL CAMERA FOR VIEWING THE SHADOW OF THE PROJECTION OF THE CONTAINER

The present invention relates to the inspection of cylindrical glass ware for malformations, dimensional variations and defects.

Glass containers are conventionally produced in an I.S. (individual section) machine from discrete gobs of molten glass. Each gob is first operated on in a blank mold, which has opposed side portions to form a parison and then the parison is blown into the finished container in a blow mold which also has opposed side portions. Where these opposed side portions of the blow mold come together a bottle seam will be formed and can usually be observed in the formed container. This seam can be unacceptably noticeable or a thin "fin" of glass can be formed at the seam and extend partially or completely along the seam. In either case, the container should be rejected upon inspection. Current inspecting techniques can not find such fins to an acceptable degree.

It is accordingly an object of the present invention to provide an inspecting machine that can to an acceptable degree determine that a fin is present so that the container can be rejected.

Other objects and advantages of the present invention will become apparent from the following portion of this specification and from the accompanying drawings which illustrate in accordance with the mandate of the patent statutes a presently preferred embodiment incorporating the principles of the invention.

Referring to the drawings.

Figure 2:
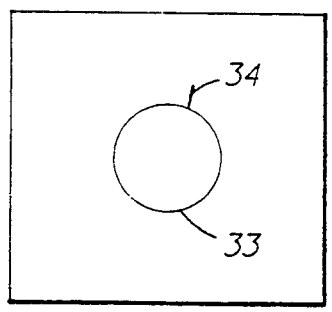
FIG. 2 is a view representing the bottle shown in FIG. 1, as seen by the camera.
Figure 3:
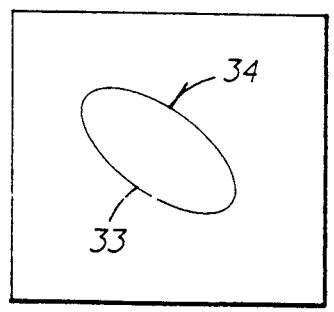
FIG. 3 is a view similar to that of FIG. 2 showing how an out of round bottle might appear.

The inspecting machine has a conveyor 10 onto which containers 12 are deposited by a feeder (not shown). Each container has a cylindrical form 13 extending vertically from the bottom of the bottle upwardly to the neck portion 14 (the axis of the bottle is vertical). The conveyor moves continuously and during its displacement the container becomes located at the illustrated inspection location where collimated light 16 passes vertically downwardly over the container. A Fresnel lens 20 receives light 19 dispersing from a short arc flash tube 18 to form the collimated light beam 16. As shown in FIGS. 2 and 3 the footprint of the collimated beam on the conveyor is selected so that for any conveyed bottle, an annular band of light will surround the bottle.

The conveyor is a one-piece, seamless, belt cast from transparent urethane and is driven by a drive system 22. It is supported by a metallic plate 23 which is covered with Teflon ® 24. Flush with the surface of the strip and secured within an opening 26, is a diffuser plate 28.

A two-dimensional camera 30 viewing vertically upwardly views the bottom of the container through the diffuser plate and sees the collimated light footprint. The sensed image is evaluated by an image processing computer 32. Such an image processing computer will evaluate the circumference (or outline, perimeter, outside edge, edge) of the image of the bottle as cast onto the diffusing surface by the collimated beam as shown in FIG. 2 and determine the presence of a fin 34 (FIG. 2) or an unacceptable out of round shape using conventional technology. As shown in FIGS. 2 and 3, the bottom of the container may appear totally black. The computer can then issue a signal to reject the bottle. The inspected container will then leave the conveyor for further processing by structure not shown. The inspected bottle is illustrated as circular in cross section in FIG. 2 but a bottle which is not intended to be circular in cross section (oval, as shown in FIG. 3, for example) can also be similarly inspected.

Figure 1:
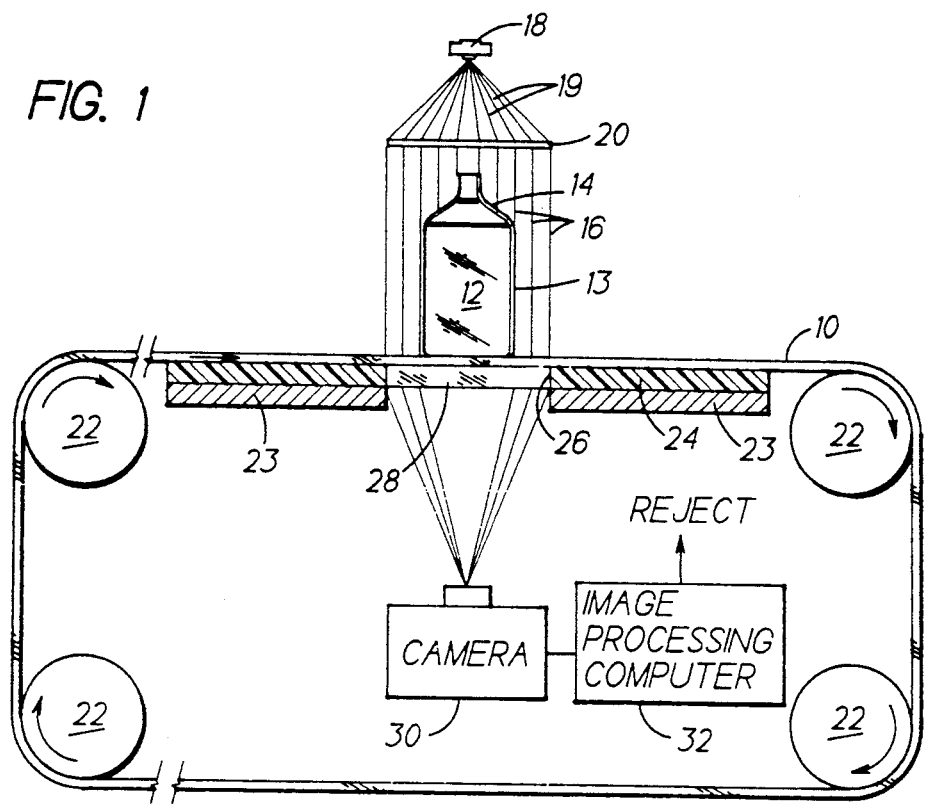
FIG. 1 is a schematic showing of an inspecting machine made in accordance with the teachings of the present invention.
Figure 4:
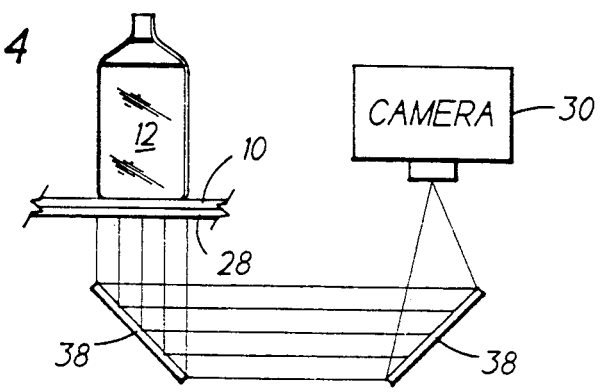
FIG. 4 is an alternate light path to the camera.

While the camera is vertically below the bottle in FIG. 1 it can be located elsewhere by the use of mirrors. For example, the camera can look vertically downwardly as shown in FIG. 4 with the use of a pair of 45° mirrors 38. Additionally, while the conveyor is shown as transparent resting on a diffusion plate, the conveyor could be the diffusion medium and the support plate could be transparent.

I claim:

1. An inspection machine for inspecting the circumference of a vertically standing container comprising
   means for conveying a vertically standing container to an inspection location,
   a diffuser plate located beneath a conveyed container at said inspection location, said diffuser plating being configured so that when the container is at said inspection location the periphery of said diffuser plate will be outwardly spaced from the circumference of the container
   means above said container for directing a beam of collimated light vertically downwardly towards said diffuser plate, said beam having a configuration selected so that when the container is located at the inspection location the periphery of said beam will be outwardly spaced from the circumference of the container,
   two dimensional camera means vertically below said diffuser plate for axially viewing the shadow of the projection of the bottom of a container on said diffuser plate at the inspection location, and
   image processing means for evaluating the circumference of the shadow of the projection of the bottom of the container viewed by said two dimensional camera and accepting or rejecting the container.

2. An inspection machine according to claim 1, wherein said conveying means displaces said container at a constant speed.

3. An inspection machine according to claim 1, wherein said conveying means comprises a transparent conveyor and said diffuser plate comprises means for supporting said transparent conveyor.

4. An inspection machine according to claim 1, wherein the container has a circular cross section.

* * * * *